United States Patent
Dittrich et al.

(10) Patent No.: US 6,527,770 B2
(45) Date of Patent: Mar. 4, 2003

(54) MEDICAL INSTRUMENT

(75) Inventors: Horst Dittrich, Immendingen (DE); Frank Doll, Dürbheim (DE); Frank Gminder, Trossingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/780,317

(22) Filed: Feb. 9, 2001

(65) Prior Publication Data

US 2001/0016740 A1 Aug. 23, 2001

Related U.S. Application Data

(63) Continuation of application No. PCT/EP99/05669, filed on Aug. 5, 1999.

(30) Foreign Application Priority Data

Aug. 10, 1998 (DE) .......................... 198 36 074

(51) Int. Cl.⁷ ............................................. A01B 18/18
(52) U.S. Cl. ........................... 606/46; 606/49; 606/170; 606/180
(58) Field of Search .............................. 606/41, 45, 46, 606/47, 49, 170, 179, 180

(56) References Cited

U.S. PATENT DOCUMENTS

| | | | | |
|---|---|---|---|---|
| 5,527,331 A | * | 6/1996 | Kresch et al. | 606/45 |
| 5,693,051 A | | 12/1997 | Schulz | |
| 6,004,320 A | * | 12/1999 | Casscells et al. | 606/49 |
| 6,214,001 B1 | * | 4/2001 | Casscells et al. | 606/41 |

FOREIGN PATENT DOCUMENTS

| | | |
|---|---|---|
| WO | WO 96/24296 | 2/1996 |
| WO | 99/05669 | 8/1999 |
| WO | WO 00/09026 | 2/2000 |

* cited by examiner

Primary Examiner—Linda C. M. Dvorak
Assistant Examiner—David M. Ruddy
(74) Attorney, Agent, or Firm—St. Onge Steward Johnston & Reens LLC

(57) ABSTRACT

The invention relates to a medical instrument for removing tissue comprising a tool at its distal end which can be supplied with high frequency power. The instrument includes an HF power terminal and an HF power supply line extending frown a proximal end region of the instrument to its distal end. In the present instrument, the HF power supply is configured as a drive shaft for rotary drive of the tool. Furthermore, contact means are provided electrically connected to the HF power terminal, which electrically contact the drive shaft.

14 Claims, 3 Drawing Sheets

MEDICAL INSTRUMENT

CROSSREFERENCE OF PENDING APPLICATION

This is a continuation of pending International Application PCT/EP99/05669, filed on Aug. 5, 1999 and claiming priority of German application DE 198 36 074, filed on Aug. 10, 1998.

BACKGROUND OF THE INVENTION

1. Field of the Invention

The invention relates to a medical instrument comprising a tool at its distal end to be supplied with high frequency (HF) power, a HF power terminal and a HF power supply line extending from a proximal end region of the instrument to its distal end, wherein the HF power supply line is configured as a drive shaft for rotary drive of the tool and wherein contact means are provided which are electrically connected to the HF power terminal and electrically contact the drive shaft.

2. Description of the Related Art

Generally such medical instruments are normally used for removing soft tissue, where the instrument comprises a substantially fixed cutting tool. HF power can be supplied to the tool, i.e a high frequency (HF) voltage or a HF current. HF current, which flows when contacting the tissue, leads to strong heating in the region adjacent to the cutting tool (electrode so that tissue is removed and the cutting location is coagulated. Thus blood vessels are closed at the same time that tissue is removed and more serious bleeding is avoided.

WO96/2429 discloses a medical instrument, namely a morselator having a proximal end and a distal end carrying an electrode where distal end is insertable into a body cavity and containment vessel for morselating resected tissue. The electrical contact to a rotating tube is provided by brushes, wherein the tube carries a ring being in sliding contact with the brushes and an electric line connecting the ring with the electrode. A further medical instrument of the same kind is disclosed in DE 2545761 A1.

SUMMARY OF THE INVENTION

In view of the above, the object of the present invention is to provide an improved medical device of the mentioned type, where the contact between the power terminal and the drive shaft is improved.

According to the present invention, a medical instrument is provided of the mentioned type, the contact means comprising a spring means configured as a U-shaped element, whose two side-pieces carry a contact element and urge the contact element with a force acting in the direction of the drive shaft.

According to the present invention, a medical instrument is provided of the mentioned type, wherein the contact means comprise spring means which urge the contact element with a force acting in the direction of the drive shaft, the contact element is guided in a contact element guide, the spring means are arranged such that a force also acts in the direction of the guide surface of the contact element guide and the guide surface is congfigured as an electrical contact surface between the contact element guide and the contact element, so that an electrical connection results between the HF power terminal and the contact element via the contact guide element.

According to the present invention, a medical instrument is provided of the mentioned type, wherein the contact means comprise a housing which receives a section of the drive shaft and in which an electrically conductive fluid is contained in fluid-tight manner, so that an electrical connection between the drive shaft, the fluid and consequently the HF power terminal results.

The advantages of the aforementioned alternatives of the present invention are that the electrical contact between the power terminal and the drive shaft is improved due to the spring means urging the contact element reliably against the drive shaft so that a good electrical connection is guaranteed.

The latter alternative has the further advantage that the heat resulting from friction of the contact element with the drive shaft rotating at high speed is distinctly reduced. The size of the contact surface is maximized through the electrically conductive fluid, which completely encloses the drive shaft in circumferential direction. In addition, this alternative has the advantage that no air gap is present between the contact element and the drive shaft.

In a further preferred embodiment of the present invention, the electrical contacting of the drive shaft is provided over a contact surface.

The advantage is that the electrical field strength in the region of this interconnection is small despite the high HF voltage, where occurrence of spark discharges is avoided. In particular, the power transmission is optimized by the contact surface being as large as possible and by a small air gap. Furthermore, high frequency electromagnetic waves arise from spark discharges, which can lead to disturbances in other electrical devices. Precisely the highly sensitive medical devices could otherwise be disturbed by such spark discharges.

In a further preferred embodiment, the electrical contacting is performed over a surface corresponding to at least a part of the circumferential region of the drive shaft.

The advantage is that a very large connection surface is realized, so that the electric field is very small. The connection surface itself can be enlarged almost arbitrarily by extension in the longitudinal direction of the drive shaft. A further advantage is that the frictional forces per unit surface are reduced, so that the wear on the contact surface is reduced and heat arising from friction is minimized. In addition, the heat generated by power transmission is distinctly reduced.

In a further preferred embodiment, the contact means comprise a displacedable contact element, which is disposed in a contact element guide and which contacts the surface of the drive shaft via a contact surface, where preferably the contact surface of the contact element is adapted to the form of the drive shaft.

This has the advantage that a contacting of the drive shaft is achieved over a larger contact surface in simple constructive manner. Depending on the configuration, the contact surface can extend over one half of the circumference of the drive shaft. Furthermore, the heat generated through friction and power transmission can be well dissipated with the contact element guide.

In a further preferred embodiment, the spring means are arranged such that the force also acts in the direction of a guide surface of the contact element guide. Preferably, the guide surface is configured as an electrical contacting surface between the contact element guide and the contact element.

This arrangement of the spring means has the advantage that the contact element is reliably biased against the guide surface of the contact element guide, so that a good electrical and thermal connection is ensured between these two parts. The HF current thus can be supplied through the guide surface and the contact element lying adjacent thereto.

In a further preferred embodiment, the contact element contains a metal, preferably copper, and is produced as a contact block.

The advantage is that the contact element has a very good electrical conductivity, where however a high abrasion resistance is maintained.

In a further preferred embodiment, the guide surface of the contact element guide is gold-plated. Preferably the circumferential region of the drive shaft engaging with the contact means is coated with a good electrically conducting material, which is also corrosion resistant, preferably gold.

The advantage is that the electrical connection between the contact means and the drive shaft is further improved, so that the danger of spark discharge is also further reduced.

Further advantages and embodiments of the invention will become apparent from the description and the appended drawings. It will be understood that the above-mentioned features and those to be discussed below are applicable not only in the given combinations but may also be present in other combinations or taken alone without departing from the scope of the present invention.

BRIEF DESCRIPTION OF THE DRAWINGS

The invention will now be described in more detail on the basis of embodiments in conjunction with the drawings.

DESCRIPTION OF THE PREFERRED EMBODIMENTS

Figure 1:
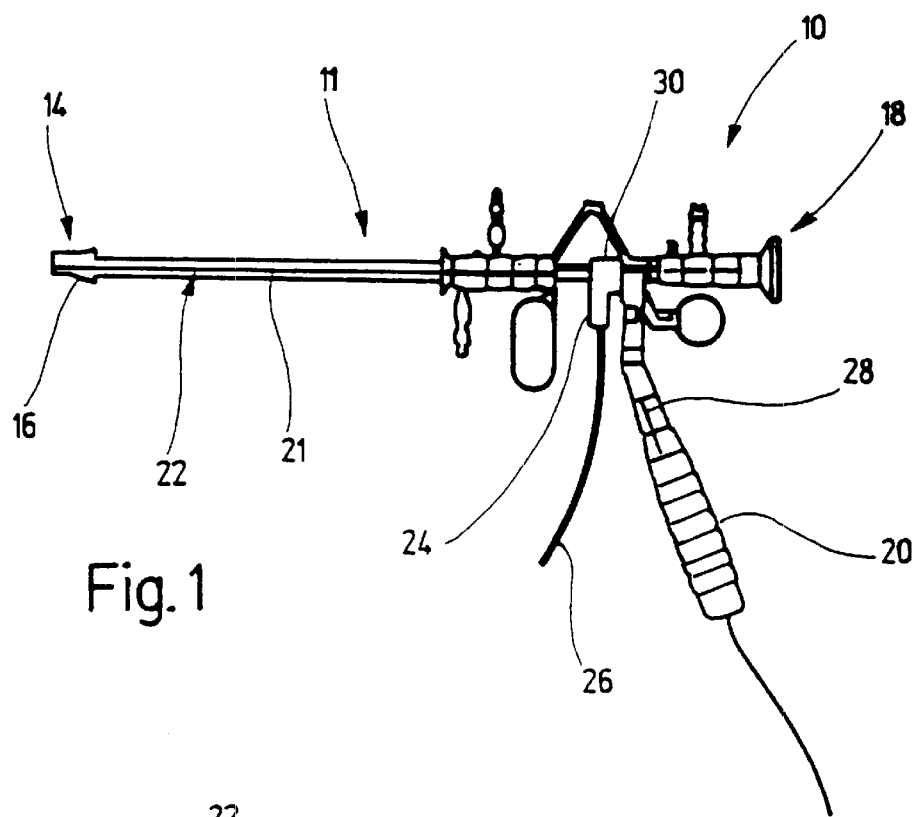
FIG. 1 shows a schematic side view of a medical instrument.

FIG. 1 gives a schematic illustration of a medical instrument, which is generally designated with reference number 10. The medical instrument is employed for example for the removal of tissue from the prostate gland and in the present embodiment is configured as an endoscopic instrument 11. The basic structure of such an instrument 11 is known and will not be described in more detail.

The instrument 11 comprises a tool 16 at its distal end 14, which is also indicated only schematically. In the present embodiment it is formed to be mountable and exchangeable, for example a cone-shaped cutting tool with an integrated electrode. In conjunction with the present invention, a cutting tool is to be understood as a tool which is generally suited for removing and coagulating tissue, for example by cutting or grinding.

The instrument 11 comprises an electric motor 20 at its proximal end 18 which drives the rotatably mounted cutting tool 16 at a preferred rotary speed of about 1000 revolutions per minute through the at least partially illustrated drive shaft 22 and a driven shaft 28. An electric terminal 24 is also provided in the region of the proximal end 18 of the instrument 11, to which an electrical line 26 can be connected. The electrical line 26 in turn is connected to a high frequency (HF) generator (not shown). Both the electric terminal 24 and the coupling means (not shown) for coupling the drive shaft 22 and the driven shaft 28 to the motor 20 are parts of a connector, which is shown in FIG. 1 with the numeral 30 and in FIG. 2 in enlarged representation. The connector 30, partially shown in FIG. 2, comprises a housing 31 in which the drive shaft 22 ends. The electrical line 26 joins into the housing 31 at a right angle to the drive shaft 22.

Contact means 40 are provided in the housing 31 including a U-shaped, electrically insulating support or carrier 41. The carrier 41 is fixed to the housing 31 and arranged such that the open end of the U-form faces the drive shaft 22. One of the two sidepieces 42a, 42b of the carrier 41 is provided with a recess 43 through which an electrical line 44 projects. The line 44 is connected on the one hand with the line 26 and on the other hand with the contacting element 45. Starting from the line 44 the contacting element 45 extends along the one sidepiece 42a and a base surface 46 of the carrier 41 and then up to the other sidepiece 42b.

The U-shaped carrier 41 receives a guide element 50 between its sidepieces 42a, 42b. The guide element 50 contacts the contacting element 45 at the two sidepieces 42a, 42b and in the region of the base surface 46. The guide element 50 is either made completely of an electrically conductive material, for example copper, or comprises only an electrically conductive coating, for example of gold, over any arbitrary, but preferably a good thermally conductive body, for example brass. The guide element 50 also has a U-shape, where a side piece 51a, 51b engage with a corresponding sidepiece 42a or 42b of the carrier 41. A base 52 of the guide element 50 faces the base surface 46 of the carrier 41 and contacts the contacting element 45, which itself engages with the base surface 46.

A block-shaped contact element 60 is displaceably mounted in a space 53 laterally defined by the two sidepieces 51a, 51b, where a contact surface 61 of the contact element 60 facing the drive shaft 22 is in electrical contact with the drive shaft 22. To ensure a reliable contact, the contact element 60 is urged by a force in the direction of the drive shaft 22. This force is preferably provided by a spring, which is supported on the one hand at the base 52 of the guide element 50 and on the other hand at the side of the contact element 60 facing the base. The spring is shown only schematically in FIG. 2 as a point and has the reference number 62.

The contact means 40 on the whole serves to supply the HF current from the line 26 through the line 44, the contacting element 45, the conductive guide element 50 and the contact element 60 to the drive shaft 22. The HF current then reaches the electrodes integrated into the tool 16, because the drive shaft 22 is made of a conductive material or at least has an electrically conductive coating and therefore serves as a voltage or current supply line 21.

Figure 2:
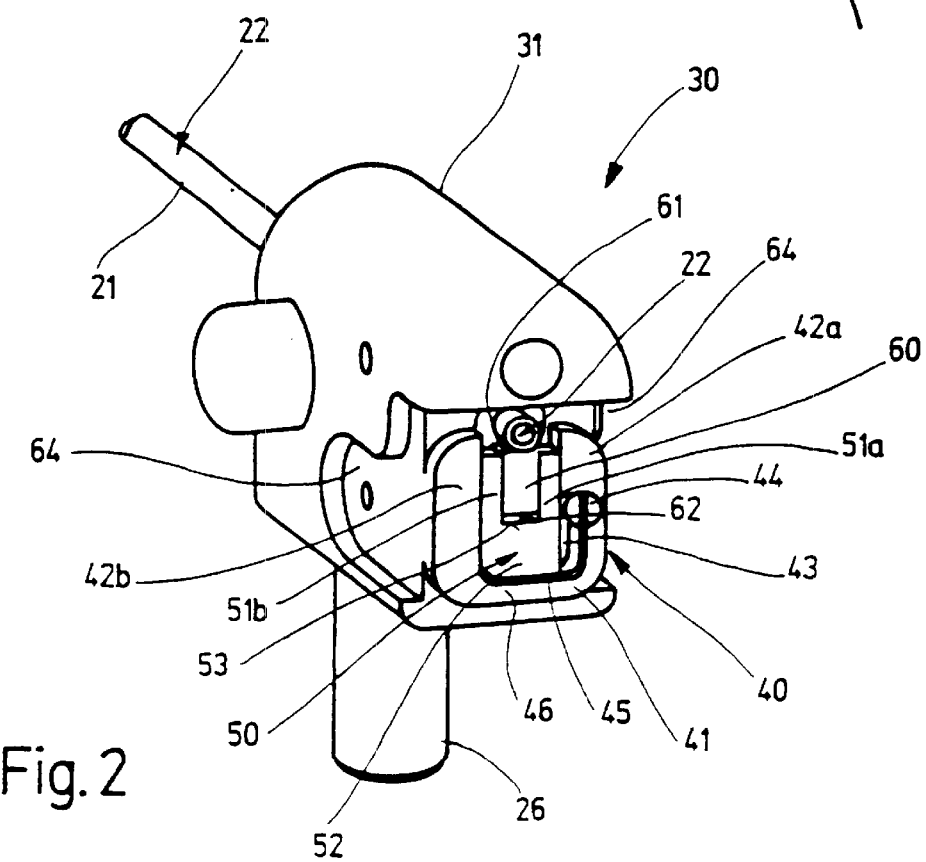
FIG. 2 shows a perspective view of a section of the medical instrument shown in FIG. 1 in the region of the contact means.

FIG. 2 shows recesses 64 provided at the side of the housing 31, which have the purpose of coupling a housing cover. The housing 31 includes a transmission device, which provides an interconnection between the driven shaft 28 and the drive shaft 22.

Figure 3:
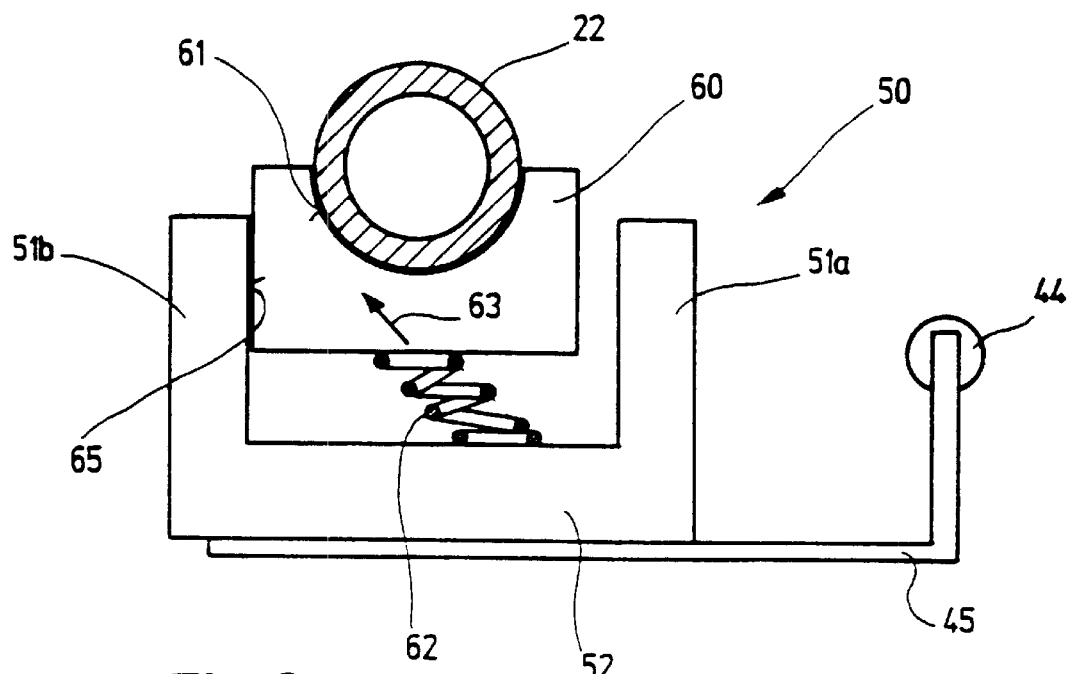
FIG. 3 shows a schematic illustration of the contact means.

With reference to FIG. 3, the guide element 50 will now be described in more detail, where the same parts shown in FIG. 2 are indicated with the same reference numbers.

As mentioned, the contact surface 61 of the contact element 60 engages with the drive shaft 22. The contact surface 61 is adapted to the outer shape of the drive shaft 22 in order to achieve the largest possible surface contact. In the present embodiment, the contact surface 61 extends in the direction transversely to the axis of the shaft 22, preferably about one half of the circumference and thus has a semi-cylindrical form. It will be understood that it is also possible to configure the contact surface 61 so that it extends over a smaller portion of the circumference.

The contact element 60 is guided by the two sidepieces 51a, 51b of the guide element 50 and is secured against tilting or pivoting about the longitudinal axis of the drive shaft 22.

As mentioned, the contact element 60 is biased by a spring force, which is indicated by the arrow 63. This force is provided by the spring 62 indicated schematically, which lies between the base 52 and the contact element 60. The spring force 63, acting at an angle with respect to the radius of the drive shaft 22, urges the contact element 60 not only with its contact surface 61 onto the drive shaft 22, but also with its side contact surface 65 against the sidepiece 51b of the guide element 50, so that a surface contact is provided.

To improve the contact between the contact element 60 and the sidepiece 51b and to protect against corrosion, the contact surface 65 is preferably coated with a good conducting layer, for example with gold. It will be understood that the contact surface 61 is coated with a highly conducting material and that the coating is also as wear resistant as possible. Thus an electric flow path results through the line 44 and the contacting element 45 to the guide element 50 and from here to the contact element 60 and the contact surface 61 and then to the drive shaft 22. The tubular drive shaft 22 then supplies the current to the tool 16. At the same time, the drive shaft 22 provides rotation of the tool 16.

Apart from the contact surface 65 between the contact element 60 and the guide element 50, the spring 62 can alternatively or additionally be configured to supply current. In this case, the spring 62 is made of an electrically conductive material or at least is coated with same, where the surfaces supporting the spring both at the contact element 60 and the side element 50 are to be coated with a material of good conductivity.

It will be understood that the spring 62 can be replaced by a plurality of individual springs comprising a spring pack. It is also possible to achieve the spring force 63 angled with respect to the radius by using two individual springs or a spring pack, where one spring acts in radial direction and the other spring is perpendicular to the contact surface 65.

Figure 4:
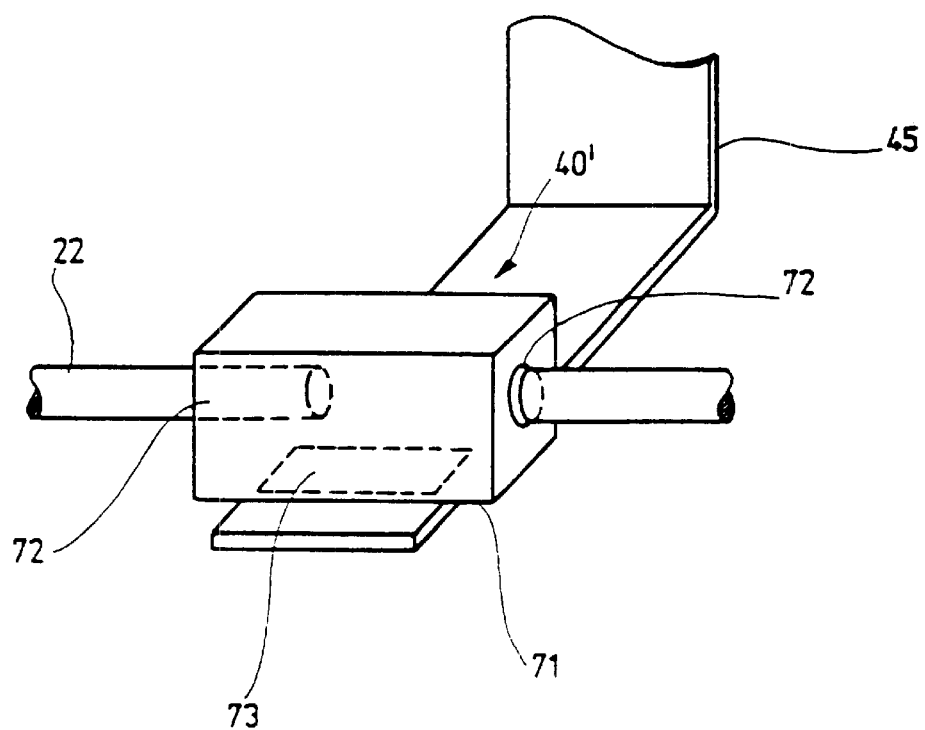
FIG. 4 shows a perspective view of the contact means according to a second embodiment.
Figure 5:
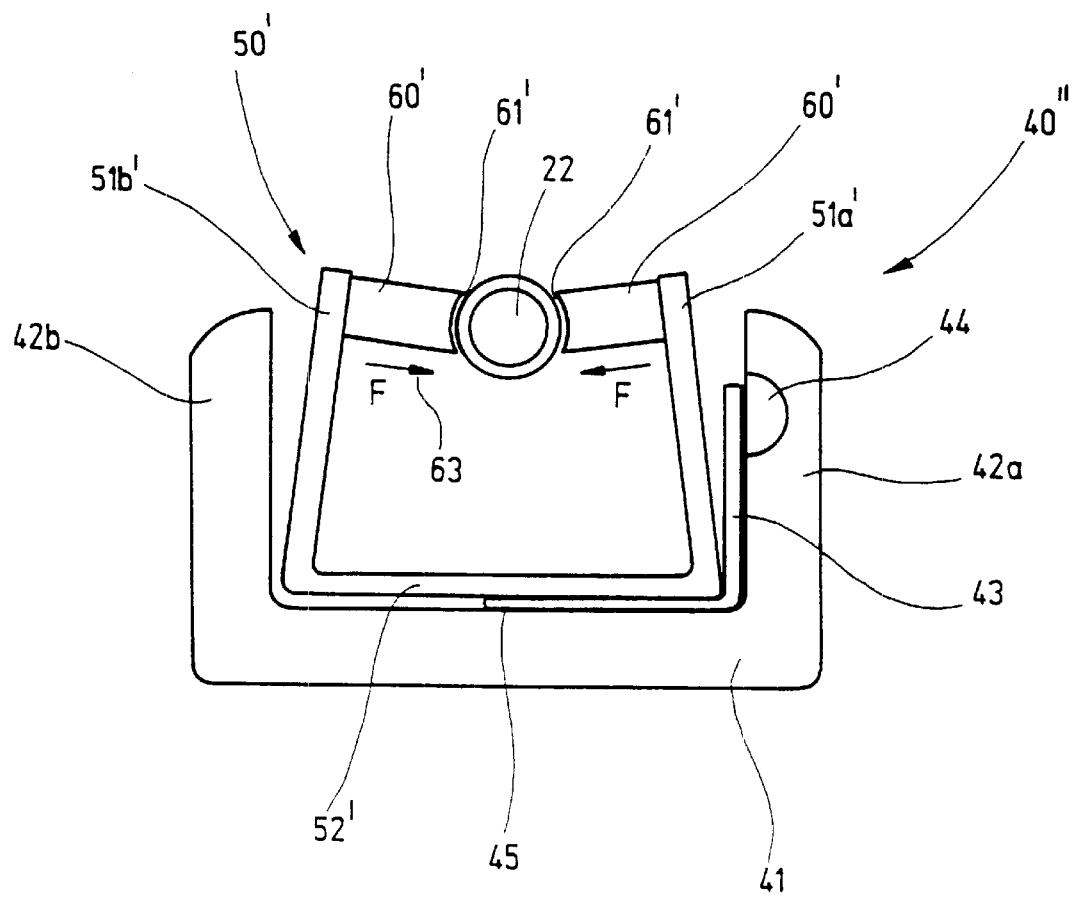
FIG. 5 shows a schematic illustration of another embodiment of the contact means used for the medical instrument shown in FIG. 1.

A further embodiment of the present invention is illustrated in FIG. 4. contact means 40' are provided comprising a cuboid shaped housing 71. In a first variation, the housing 71 is completely penetrated by the drive shaft 22, where the necessary shaft sealings are provided at both opening 72 to make the housing 71 fluid-tight. The housing 71 is filled with a fluid, preferably liquid metal, for example mercury, which has good electrical conductivity.

By proper selection of the amount of fluid, the section of the drive shaft 22 within the housing 71 is completely surrounded by fluid. In a preferred second variation, the drive shaft 22 terminates within the housing 71, as indicated with dashed lines, so that only the side of the housing with one opening 71 need be provided with a shaft sealing. In both variations, the housing 71 comprises a contact surface 73 which establishes an electrical connection between a contacting element 45 and the fluid located within the housing 71.

It will be understood that other embodiments are also possible which allow contacting, preferably over a larger surface of a drive shaft. The large surface contact has the advantage that spark discharges caused by higher electric field strengths are avoided. At the same time, this counteracts degradation of the drive shaft 22 due to such spark discharges.

The two embodiments are configured for monopolar applications. It will be understood that the invention is also applicable in medical instruments with bipolar applications. In this case, two contact means 40 can be employed, where the two HF voltage supply lines can be configured for example as two coaxially arranged shafts.

What is claimed is:

1. Medical instrument comprising a tool at its distal end to be supplied with high frequency (HF) power, a HF power terminal and a HF power supply line extending from a proximal end region of the instrument to its distal end, wherein the HF power supply line is configured as a drive shaft for rotary drive of the tool and wherein contact means are provided which are electrically connected to the HF power terminal and electrically contact the drive shaft, characterized in that the contact means comprise a spring means configured as a U-shaped element, whose two sidepieces carry a contact element and urge the contact element with a force acting in the direction of the drive shaft.

2. Medical instrument of claim 1, wherein the electrical contacting is configured as surface contact.

3. Medical instrument of claim 2, wherein the electrical contacting is configured as a surface contact over at least a partial circumference of the drive shaft.

4. Medical instrument of claim 1, wherein the contact element engages with a contact surface over a surface of the drive shaft.

5. Medical instrument of claim 4, wherein the contact surface of the contact element is adapted to the shape of the drive shaft.

6. Medical instrument of claim 1, wherein the spring means consist of an electrically conductive material and an electrical connection is made possible between the HF power terminal and the contact element.

7. Medical instrument of claim 1, wherein the contact element contains a material of good electrical conductivity.

8. Medical instrument of claim 1, wherein the circumferential region of the drive shaft engaging with the contact means is coated with a resistant material having a good conductivity.

9. Medical instrument comprising a tool at its distal end to be supplied with high frequency (HF) power, a HF power terminal and a HF power supply line extending from a proximal end region of the instrument to its distal end, wherein the HF power supply line is configured as a drive shaft rotary drive of the tool and wherein contact means are provided which are electrically connected to the HF power terminal and electrically contact the drive shaft, characterized in that the contact means comprise a housing which receives a section of the drive shaft and in which an electrically conductive fluid is contained in fluid-tight manner, so that an electrical connection between the drive shaft, the fluid and consequently the HF power terminal results.

10. The medical instrument of claim 7, wherein the material is copper.

11. The medical instrument of claim 7, wherein the material forms a contact block.

12. The medical instrument of claim 8, wherein the material is gold.

13. Medical instrument comprising a tool at its distal end to be supplied with high frequency (HF) power, a HF power terminal and a HF power supply line extending from a proximal end region of the instrument to its distal end, wherein the HF power supply line is configured as a drive shaft for rotary drive of the tool and wherein contact means are provided which are electrically connected to the HF power terminal and electrically contact the drive shaft, characterized in that the contact means comprise spring means which urge the contact element with a force acting in the direction of the drive shaft, further comprising a contact element guide in which the contact element is disposed, which guide has a guide surface that is an electrical contact surface between the contact element guide and the contact element, such that an electrical connection exists between the HF power terminal and the contact element, which contact element is biased against the guide surface by the spring means, which spring means are arranged such that a force also acts in the direction of the guide surface.

14. Medical instrument of claim 13, wherein at least the guide surface of the contact element guide is gold-plated.

* * * * *